(12) United States Patent
Qazi et al.

(10) Patent No.: US 6,905,876 B2
(45) Date of Patent: Jun. 14, 2005

(54) **METHODS AND COMPOSITIONS FOR IN VITRO GERMINATION AND PROPAGATION OF *POLYGONATUM CIRRHIFOLIUM* ROYLE**

(75) Inventors: Ghulam Nabi Qazi, Jammu (IN); Surrinder Kumar Lattoo, Jammu (IN); Avtar Krishan Dhar, Jammu (IN); Paresh Purohit, Jammu (IN); Ravinder Kumar Raina, Jammu (IN); Rekha Sapru Dhar, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/998,573

(22) Filed: Nov. 16, 2001

(65) Prior Publication Data

US 2003/0100109 A1 May 29, 2003

(51) Int. Cl.⁷ .................................................. C12N 5/00
(52) U.S. Cl. ........................................ 435/430; 435/431
(58) Field of Search .................................. 435/430, 431

(56) References Cited

PUBLICATIONS

Lattoo, S.K. et al., *Current Science*, 81(11): 1414–1417 (2001).
Choi, Y.E. et al., *Plant Cell Rep.*, 18(6): 493–499 (1999).
Nhut, D.T., *Plant Cell Rep.*, 17(12): 913–916 (1998).
Clark, M., ed., *Plant Molecular Biology*, Springer Verlag (1997).
Jones, P., ed., *Plant Molecular Biology*, John Wiley & Son, Ltd. (1997).
Gelvin, S.B., Schilperoort, R.A., Verma, D.P.S., eds., *Plant Molecular Biology Manual, 2nd edition*, Klewer (1994).
Chee, P.P., *Hort Science*, 29(6): 695–697 (1994).
Buchheim J.A.T. et al., *Plant Cell Tissue Organ Culture*, 36(1): 35–43 (1994).
Gingas, V.M. and Lineberger, R.D., *Plant Cell Tissue Organ Culture*, 17(3): 191–203 (1989).
Thomas, J.A. and Meyer, M.M., *In Vitro* 23(3, pt. 2): 70A (1987).
Sengupta, J. and Sen, S., *Current Science*, 56(24): 1287–1289 (1987).
Baskin, J.M. and Baskin, C.C., *Amer. J. Bot.*, 72(2): 185–190 (1985).
Singh, U. et al., *Economics Plants of India*, IARI, New Delhi, 180 (1983).
Shah, N.C., "An Assessment of Threatened Plants of India," *Botanical Survey of India*, Calcutta, 40–49 (1983).
Black, M., *Israil J. Bot.* 29: 181–192 (1980/1981).
Lal, V.K. et al., *Indian Drugs*, pp. 286–287 (Jun., 1980).

Nikolaeva, M.G., "Factors Controlling the Seed Dormancy Pattern" in *The Physiology and Biochemistry of Seed Dormancy and Germination*, (A.A. Khan, ed.), 51–74, North–Holland Biomedical Press, Amsterdam (1977).
Jones, R.L. and Stoddart, J.L., "Gibberellins and Seed Germination" in *The Physiology and Biochemistry of Seed Dormancy and Germination*, (A.A. Khan, ed.), 77–109, North–Holland Biomedical Press, Amsterdam (1977).
*Wealth of India Raw Materials*, 9: 365, CSIR, New Delhi (1976).
Dure, L.S. III, *Ann. Rev. Plant Physiol.*, 26: 259–278 (1975).
Brahmashankar, M. and Rupalalji, V., *Bhavaprakasha Nighantu*, pt. 1, Chowkhamba Sanskrit Sansthan, Varanasi, sloka 120–122 (1972).
Villiers, T.A., in *Seed Biology* (T.T. Kozlowski, ed.) vol. II, 220–281 (1972).
Stokes, P., *Encyclop. Plant Physiology*, XV/2: 746–803 (1965).
Murashige, T. and Skoog, F., *Physiol. Plant*, 15: 433–497 (1965).

*Primary Examiner*—Andrew Wang
*Assistant Examiner*—Annette H Para
(74) *Attorney, Agent, or Firm*—Baker Botts L.L.P.

(57) ABSTRACT

The present disclosure relates to methods and compositions for in vitro cultivation of species of *Polygonatum*, e.g. *Polygonatum cirrhifolium* Royle. The disclosure provides culture media comprising MS basal culture media and plant hormones, preferably selected from the group consisting of gibberellic acid ($GA_3$), 6-benzyl-aminopurine (BAP), and naphthalene acetic acid (NAA). The disclosure provides methods of in vitro cultivation of *Polygonatum* comprising contacting *Polygonatum* seeds with a first medium comprising MS basal culture medium and $GA_3$, upon emergence of a hypocotyl, transferring this primary explant to a second medium comprising MS basal culture medium, BAP, and NAA, and upon emergence of a first foliage leaf, transferring this secondary explant to a third medium comprising MS basal culture medium, BAP, NAA, and gibberellic acid ($GA_3$). The methods and compositions of the disclosure are capable of inducing and/or supporting uniform germination in less than about 90 days, synchronized development of epicotyl, coleoptile, and radicle, termination of epicotyl dormancy and combinations thereof. The present disclosure relates to the novel culture medium compositions, said compositions comprising Murashige and Skoog (MS), a basal culture medium, varied concentrations of plant hormones, and other additives, leading to extraordinarily fast and synchronized in vitro induction of germination and release of epicotyl dormancy in *Polygonatum cirrhifolium* Royle, an endangered medicinal plant species and a method for faster in vitro propagation of *Polygonatum cirrhifolium* Royle.

41 Claims, 8 Drawing Sheets

(8 of 8 Drawing Sheet(s) Filed in Color)

METHODS AND COMPOSITIONS FOR IN VITRO GERMINATION AND PROPAGATION OF *POLYGONATUM CIRRHIFOLIUM* ROYLE

FIELD OF THE INVENTION

The present invention relates to novel culture media compositions for extraordinarily fast in vitro induction of germination and release of epicotyl dormancy in *Polygonatum cirrhifolium* Royle, an endangered medicinal plant species. In some embodiments of the invention, the compositions comprise Murashige and Skoog (MS), a basal culture medium, varied concentrations of plant hormones, and other additives. The present invention also relates to methods of rapid in vitro propagation of *Polygonatum cirrhifolium* Royle.

BACKGROUND OF THE INVENTION

Over 60 species of *Polygonatum* grow in the wild in North America, Europe, Asia, Japan and Siberia. *Polygonatum* is in the lily family, *Liliaceae*. Some members of this genus have long generation times. For example, *Polygonatum cirrhifolium* Royle may take 3–5 years to go from seed to seed in the wild.

*Polygonatum cirrhifolium* Royle is an important medicinal plant of temperate Himalayas (*Wealth of India Raw materials*, 1976, 9, 365, CSIR, New Delhi). Its rhizomes constitute an important ingredient of Astavarga, a group of eight drugs used extensively in Indian system of medicine mainly as tonics and aphrodisiacs (Misra, B. and Vaishya, R. 1972, *Bhavaprakasha Nighantu*, pt.1, Chowkhamba Sanskrit Santhan, Sloka 120–122). These attributes arise from the presence of steroidal saponins and polysaccharides in the rhizomatous root-stock of the plant. The plant is also useful in the preparation of cosmetics, skin tonic and as a vegetable (Singh, U. et al., 1983, In: *Economic plants of India*, IARI, new Delhi, 180). Exploitation of *Polygonatum cirrhifolium* Royle from wild habitats for its medicinal properties has led to its being placed on the list of threatened species (Shah, N. C. 1983, In: *An assessment of threatened plants of India*, Botanical Survey of India, Calcutta, 40–49).

According to the seed dormancy classification of Mikolaeva (Mikolaeva, M. G. 1977, In *The physiology and biochemistry of seed dormancy and germination*, A. A. Khan (ed.), 51–74. North Holland Publ. Co., Amsterdam, N.Y. and oxford), epicotyl dormancy is one of seven types of morphophysiological dormancy.

Morphophysiologically dormant seeds have rudimentary embryos that require cold or some combination of warm or cold stratification to initiate embryo growth (Baskin, J. M. and Baskin, C. C. 1985, *Amer. J. Bot.*, 72(2), 185–290). These requirements can be satisfied or overcome in vitro by providing plant growth regulators and inorganic and organic nutrients together with appropriate thermal and photoperiodic conditions.

Immature embryos can often be induced to germinate by supplying nutrients (Dure, L. S. III, 1975 *Ann. Rev. Plant Physiol.* 26, 259–278). Such stimulatory effects of gibberillic acids (GA) on germination of both dormant and non-dormant seeds has been widely reported (Lang, A. 1965, 848–893; Stokes, P. 1965, 746–803, *Encyclop. Plant Physiology.* XV/2; Villiers, T. A. 1972, In: *Seed biology* (T. T. Kozlowski, ed.) Vol II, 220–281; Black, M. 1980/1981, *Israil J. Bot.* 29: 181–192).

Gibberillins are known to activate hydrolytic enzymes, especially in darkness. This results in an increase in the osmotic content of the seed, increasing its water potential and giving the hypocotyl power to break through the seed coat. In epicotyl dormancy gibberellins have been found to be potent substitute for the cold stratifications, resulting in the maturation of the embryo.

The literature is replete with references where in vitro approaches have been successfully used to release various forms of physiological dormancy employing various growth enhancing agents, especially gibberillic acid ($GA_3$), 6-benzyl-aminopurine (BAP) and naphthalene acetic acid (NAA). ( Chee, P. P. 1994. *Hort Science*, 29 (6), 695–97; Nhut, D. T. 1998. *Plant Cell Rep.*, 17(12), 913–16; Choi, Y. E. et al., 1999, *Plant Cell Rep.*, 18(6), 493–99 1994, *Hort Science*, 29(6), 695–97; Buchheim J. A. T. 1994 *Plant Cell Tissue Organ Culture*, 36(1), 35–43; Gingas, V. M. and Lineberger, R. B. 1989. *Plant Cell Tissue Organ Culture*, 17(3), 191–203, Thomas, J. A. and Meyer, M. M. 1987. *In vitro* 23, 3pt 2, 70 A).

The broader phenological pattern of germination in this particular species was studied under laboratory and field conditions for three years of growth. The seeds of *P. cirrhifolium* were observed to exhibit epicotyl dormancy and to have separate stratification requirements for hypocotyl, epicotyl and radicle emergence. It was also found that the epicotyl requires one, two or more stratifications to release first foliage leaves. Natural germination of *P. cirrhifolium* is protracted, meager, and asynchronous. *P. cirrhifolium* plants take 3 to 5 years to grow to full size when raised from seeds. The inventors are not aware of any published reports where *P. cirrhifolium* germination has been induced by in vitro or other means.

SUMMARY OF THE INVENTION

The present invention relates to methods and compositions for in vitro cultivation of species of *Polygonatum*, e.g. *Polygonatum cirrhifolium* Royle. The invention provides culture media comprising MS basal culture media and plant hormones, preferably selected from the group consisting of gibberellic acid ($GA_3$), 6-benzyl-aminopurine (BAP), and naphthalene acetic acid (NAA). The invention provides methods of in vitro cultivation of *Polygonatum* comprising contacting *Polygonatum* seeds with a first medium comprising MS basal culture medium and $GA_3$, upon emergence of a hypocotyl, transferring this primary explant to a second medium comprising MS basal culture medium, BAP, and NAA, and upon emergence of a first foliage leaf, transferring this secondary explant to a third medium comprising MS basal culture medium, BAP, NAA, and gibberellic acid ($GA_3$). The methods and compositions of the invention are capable of inducing and/or supporting uniform germination in less than about 90 days, synchronized development of epicotyl, coleoptile, and radicle, termination of epicotyl dormancy and combinations thereof.

BRIEF DESCRIPTION OF THE DRAWINGS

The patent application file contains at least one drawing executed in color. Copies of this patent or patent application publication with color drawing(s) will be provided by the Office upon request and payment of the necessary fee.

DETAILED DESCRIPTION OF THE INVENTION

Figure 1:
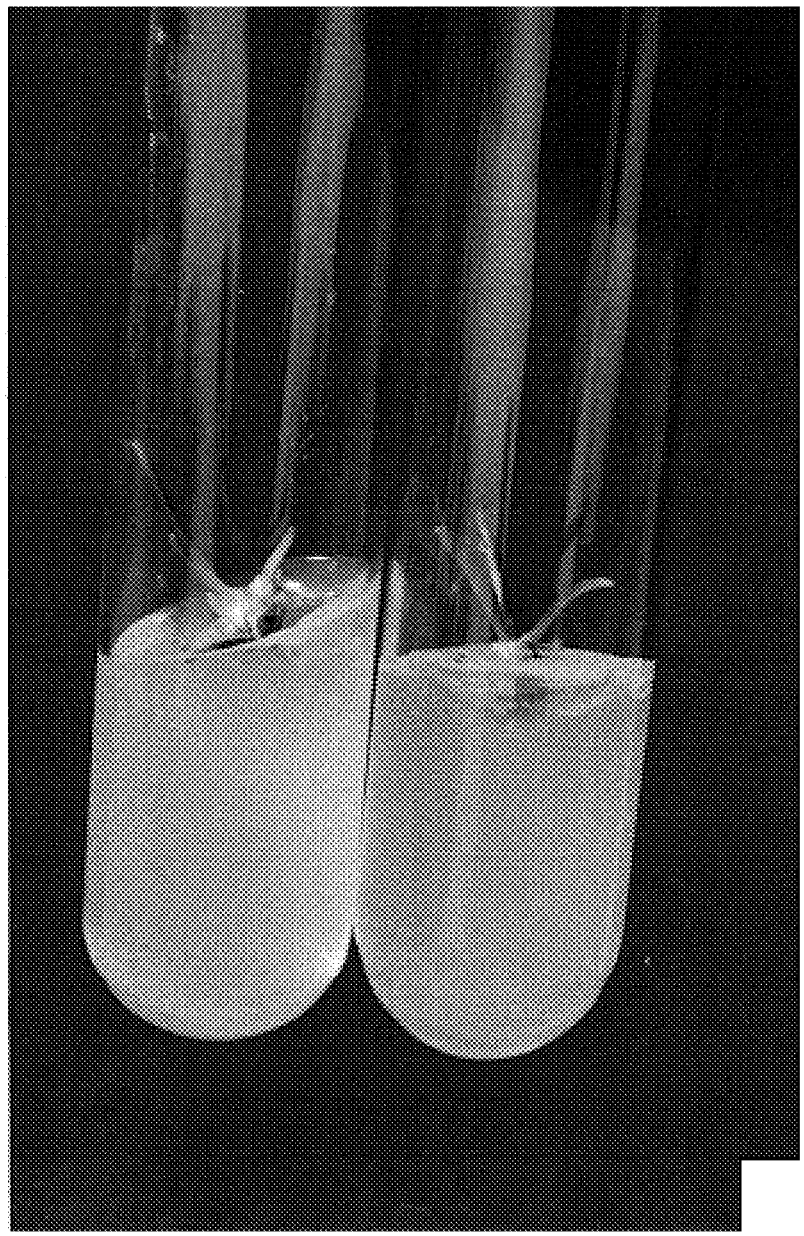
FIG. 1. Induction of germination in *Polygonatum cirrhifolium* Royle marked by the emergence of hypocotyl.

In the context of this disclosure, absent a contrary indication, the following terms shall be defined as indicated.

Cultivate—To grow, foster growth or propagate. The term is not limited with respect to developmental stage, i.e. refers to progression from any developmental stage to any other developmental stage.

Emerge—To become visible usually to the naked eye, but may include visibility aided by a dissecting scope (about 10×).

Explant—A plant at any development stage, substantially free of contaminating microorganisms, suitable for culture in a nutrient medium. A primary explant is a seed bearing a newly emerged hypocotyl. A secondary explant is a seedling bearing a newly emerged first leaf. A tertiary explant is a plant bearing axillary buds and/or axillary leaves.

Fast or Rapid—According to the invention, "rapid" or "fast" germination means germination in less than 90 days. In some nonlimitling embodiments of the invention, in vitro germination occurs in about 81 days. This contrasts with the up to 8 to 10 months required for germination in the wild.

Germination—The initial stages in the growth of a seed to form a seedling. The embryonic shoot (plumule) and embryonic root (radicle) emerge and grow upwards and downwards respectively. Food reserves for germination come from endosperm tissue within the seed and/or from the seed leaves (cotyledons).

Hypocotyl—Portion of an embryo or seedling below the cotyledons, which is a transitional area between stem and root.

In the wild—Cultivation and/or propagation "in the wild" primarily refers to outdoor growth of *Polygonatum* plants in an environment similar to *Polygonatum* 's native habitat substantially free of human manipulation. However, this term encompasses any environment wherein at least one or more of the following factors is not and/or cannot be controlled: temperature, humidity, photoperiod, light intensity, and exposure to microorganisms, herbivores, or pathogenic organisms.

Induce—To stimulate or support a response.

MS basal culture medium—Culture medium described by Murashige, T. and Skoog, F. 1965. Physiol Plant 15: 433–497 and variants thereof known in the art and MS basal culture medium I, MS basal culture medium II.

MS basal culture medium I—This comprises 2.2 g/L $NH_4NO_3$, 2.0 g/L $KNO_3$, 0.44 g/L $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2$ $MoO_4.2H_2O$, 0.025 mg/L $CuSO_4.5H_2O$, 0.025 mg/L $CoCl_2.6H_2O$, 250 mg/L myo-inositol, 0.5 mg/L nicotinic acid, 0.5 mg/L pyridoxine HCl, 3 mg/L thiamine HCl, 2 mg/L glycine, and 30 g/L sucrose. Variations of the indicated concentrations, if any, are preferably less than 5%.

MS basal culture medium II—This comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2$ $MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

Synchronous—Epicotyl dormancy, coleoptile dormancy, and radicle dormancy are all broken or terminated at substantially the same time. Growth and development of these organs usually ensues.

Time—Period following initial contact with a media. For example, "days" may refer to the time after seeds are first contacted with a germination media or to the time after seedlings are first contacted with leafing media.

General Remarks

The instant invention relates to in vitro germination, cultivation, and/or propagation of species of the genus Polygonatum, preferably *Polygonatum cirrhifolium*, more preferably *Polygonatum cirrhifolium* Royle. The present invention is not limited to any particular variety or genotype but can be applied to genetically diverse and composite seeds of *P. cirrhifolium*. The methods and compositions of the invention may be used for other species of *Polygonatum* including, inter alia, *oppositifolium* Royle and *verticillatum* L.

The concentration ranges of MS culture medium and hormones provided by the instant invention have been observed to be of critical importance. The order in which the media are used has also been observed to be of critical importance. The other growth parameters have also been observed to be of critical importance.

Germination Time, Uniformity, and Consistency

The present invention provides methods and compositions for extraordinarily fast and synchronized in vitro induction of germination in *P. cirrhifolium* Royle. In some embodiments, the methods and compositions of the invention are capable of inducing or supporting germination in less than 90 days, more preferably in less than 60 days. In some embodiments of the invention, germination occurs in from about 7 days to about 53 days. The methods and compositions of the invention may be used for initiating faster germination, with only 81 days in vitro, to achieve the same.

In some embodiments, the methods and compositions of the invention are capable of inducing or supporting a germination rate greater than 65%, preferably greater than 75%. In some embodiments of the invention, the germination rate is from about 78% to about 100%.

In some embodiments of the invention, the methods and compositions provided may be used for reliable and uniform germination. In some embodiments of the invention, the methods and compositions of the invention may be used for uniform and high germination rates.

Synchronous Release of Dormancy

In some embodiments, the methods and compositions of the invention are capable of inducing or supporting a synchronous release of epicotyl dormancy, coleoptile dormancy, and radicle dormancy.

In some embodiments, the methods and compositions of the invention are capable of inducing or supporting the production of a first foliage leaf by more than about 65% of primary explants, preferably more than 75%. A first foliage leaf may appear on from about 65% to about 86% of primary explants.

In some embodiments of the invention, each secondary explant has an average number of from about 2.7 to about 4 leaves. In some embodiments of the invention, the length of the leaves on each secondary explant averages between about 3 cm and about 6 cm.

Break Epicotyl Dormancy

The invention provides in vitro methods of breaking epicotyl dormancy in *Polygonatum cirrhifolium*. The invention provides methods by which epicotyl dormancy in *Polygonatum cirrhifolium* may be released under in vitro conditions within a short time with substantially no intervening period of dormancy. In the wild, epicotyl dormancy may last 3–5 years when plants are raised from seeds. The release of epicotyl dormancy is marked in some embodiments by the emergence of rosette leaves and differentiation of de novo axillary buds and their sprouting.

Cultivation on compositions of the invention may be the first step towards release of the epicotyl dormancy.

Other Features

The invention provides methods and compositions for rapid in vitro multiplication of *Polygonatum cirrhifolium* Royle. These methods and compositions may shorten or eliminate the dormancy period. The invention contemplates use of these methods and compositions for commercial bulk production of this plant. The invention provides methods and compositions that make it possible to produce gram or even kilogram quantities of *Polygonatum* plant material from seeds in less than about 3 to six months.

In some embodiments, the methods and compositions of the invention may be used for breeding and/or selecting elite types of *Polygonatum*.

The methods and compositions of the invention may be used to raise large populations of genetically heterogeneous *Polygonatum cirrhifolium* Royle seedlings for in-situ and ex-situ conservation of this threatened species. The methods and compositions of the invention may also be used to cultivate *P. cirrhifolium* anywhere in the world during any season. Fast in vitro propagation of *P. cirrhifolium* according to the invention may allow wider utilization of its medicinal properties.

In some embodiments of the invention, BAP and NAA have stimulatory effect on the induction of shootlets in the axillary buds of *Polygonatum oppositifolium* Royle and *P. verticillatum* L.

Materials

The culture media compositions of the invention comprise Murashige and Skoog (MS) basal culture medium, varied concentrations of plant hormones, and other additives. Plant hormones may be selected from the group consisting of gibberillic acid ($GA_3$), BAP and NAA. Additives may include agar.

In some embodiments of the invention, a first or "germination" medium comprises MS basal culture medium and from about 10 mg/L to about 100 mg/L Gibberellic acid ($GA_3$). These compositions are capable of inducing or supporting a germination rate of about 65% to about 98% in from about 7 days to about 53 days. These compositions are also capable of inducing or supporting the release of epicotyl, coleoptile and/or radicle dormancy in from about 78% to about 100%. These compositions are further capable of inducing or supporting the synchronous release of epicotyl, coleoptile and radicle dormancy from about 11 to about 18 days.

In some preferred embodiments, a first medium comprises MS basal culture medium and about 50 mg/L $GA_3$ and is capable of inducing or supporting a germination rate of about 98% in from about 7 days to about 23 days. In some preferred embodiments, a first media comprises MS basal culture medium and from about 50 mg/L to about 100 mg/L $GA_3$ and is capable of inducing or supporting release of epicotyl, coleoptile and radicle dormancy in about 100% of plants grown on this media in from about 11 to about 14 days.

In some embodiments of the invention, a second or "leafing" medium comprises MS basal culture medium, from about 3 mg/L to about 6 mg/L of BAP, and from 0.5 mg/L to about 1.0 mg/L NAA. These compositions are capable of inducing or supporting the release of a first foliage leaf from about 65% to about 85% of epicotyl dormant explants. The mean number of leaves per secondary explant ranges from about 2.7 to about 4. Leaf length ranges from about 3 cm to about 6 cm.

In some preferred embodiments, a second medium comprises MS basal culture medium, from about 3 mg/L to about 6 mg/L of BAP, and about 1.0 mg/L of NAA. These compositions are capable of inducing or supporting the release of a first foliage leaf from about 86% of secondary explants. The mean number of leaves per secondary explant is about 3.4. The mean leaf length is about 6 cm.

In some embodiments of the invention, a third or "budding" medium comprises MS basal culture medium, about 2.0 mg/L BAP, about 1.0 mg/L NAA, and from about 5 mg/L to about 20 mg/L ($GA_3$). These compositions are capable of inducing or supporting the release of axillary buds in from about 70% to about 100% epicotyl dormant explants. The mean number of axillary buds per secondary explant ranges from about 6 to about 12. From about 45% to about 98% of these axillary buds produce leaves.

In some preferred embodiments, a third medium comprises MS basal culture medium, about 2 mg/L of BAP, about 1.0 mg/L of NAA, and from about 15 mg/L to about 20 mg/L $GA_3$. These compositions are capable of inducing or supporting the release of axillary buds from about 100% of secondary explants. The number of axillary buds initiated on these media ranges from about 9 to about 12 and from about 77% to about 98% of these axillary buds produce leaves.

In some embodiments of the invention, MS basal culture medium is preferably MS basal culture medium I.

In some embodiments, the invention provides a synergistic formulation of a culture medium for the induction of germination and release of epicotyl, coleoptile and radicle in the dormant seeds of *Polygonatum cirrhifolium* Royle by placing seeds on a culture medium comprising MS basal culture medium I, 7.5 g/L agar, and from about 2 to about 50 mg/L gibberillic acid ($GA_3$) and incubating at 30° C. (±2° C.) and diurnal temperature regime of 30/20° C. (±2° C.) under continues darkness. This results in the induction of germination as indicated by the emergence of hypocotyl.

The concentration ranges of MS culture medium and hormones provided by the instant invention have been observed to be of critical importance in some embodiments. The order in which the media are used has also been observed to be of critical importance in some embodiments. The other growth parameters have also been observed to be of critical importance in some embodiments.

The present invention relates to synergistic formulations of culture media for the in vitro release of epicotyl dormancy in *Polygonatum cirrhifolium* Royle as indicated by the release of rosette of leaves, differentiation of de novo axillary buds, and sprouting of these buds. Germinated seeds with epicotyl, coleoptile and radicle are placed on one of two culture media. The first or "Set 1" medium comprises MS basal culture medium II, 7.0 g/L agar, from about 1 mg/L to about 6 mg/L of BAP, and from about 0.1 mg/L to about 1.0 mg/L NAA. The second or "Set 2" medium comprises MS basal culture medium II, 7.0 g/L agar, about 3 mg/L BAP, about 1.0 mg/L NAA, and from about 1 to about 20 mg/L gibberellic acid (GA3). Secondary explants consisting of epicotyl with emergent coleoptile and radicle obtained from the in vitro germinated seeds were transferred aseptically to one of these same two culture media.

In still another embodiment of the present invention, synergistic formulations of culture media for the in vitro release of epicotyl dormancy in *Polygonatum cirrhifolium* Royle indicated by the release of rosette of leaves and differentiation of de novo axillary buds and their sprouting by placing in vitro germinated seeds with epicotyl, coleoptile and radicle on Murashige and Skoog's, (MS) basal nutrient culture medium and 100 mg/L myo-inositol, 0.5 mg/L nicotinic acid, 0.5 mg/L pyridoxine HCl, 0.1 mg/L thiamine HCl, 2 mg/L glycine, 30 g/L sucrose, 7.0 g/L agar, supplemented with 1–6 mg/L of 6-benzyl-aminopurine (BAP) and 0.1–1.0 mg/l naphthalene acetic acid (NAA) or 3 mg/L of BAP, 1.0 mg/L NAA and 1–20 mg/L of gibberellic acid (GA3).

Methods

The invention contemplates the use of standard techniques related to in vitro germination and cultivation of plants. See e.g. Gelvin S B, Schilperoort R A, Verma D P S, eds., *Plant Molecular Biology Manual, 2nd edition*, Klewer 1994; Clark M, ed., *Plant Molecular Biology*, Springer Verlag 1997; Jones P, ed., *Plant Molecular Biology*, John Wiley & Son Ltd 1997. One of ordinary skill in the art will appreciate that techniques developed for in vitro cultivation and propagation of lily, Arabidopsis, tobacco, rice and other plants may be useful for practicing the instant invention. Unless otherwise specified, all in vitro methods were performed using appropriate aseptic techniques known to those of ordinary skill in the art, such as use of Laminar air flow.

*Polygonatum* berries may be collected, preferably when ripe, from plants grown in vitro or in the wild. Seeds may be removed from the berries after about 15 days of dehydration at room temperature. Seeds may be washed with tap water and a small amount of Tween-20™ (sorbitan mono-9 octadecenoate poly(oxy-1,1-ethanedlyl), e.g. 1–2 drops. Alternatively or additionally, seeds may be washed three times in distilled water. Seeds may be sterilized, e.g. after washing, by exposure to 0.1% mercuric chloride ($HgCl_2$) for about 3 minutes.

Sterilized seeds may be placed in sterile disposable plastic Petri plates (e.g. 10 cm×2 cm) containing semi-solid culture medium (e.g. comprising 7.5% agar). The medium may be adjusted to a pH of about 5.8, preferably exactly 5.8, by titration with an acid, e.g. 1 N HCl, or a base, e.g. 1 N NaOH. Media maybe sterilized by autoclaving at 121° C. and 15 psi for 20 minutes or any other comparable method known in the art.

Following sterilization media may be cooled, for example in a water bath at a temperature that is higher than the gelling temperature of the semisolid substrate, e.g. agar or agarose. For example, the temperature should be 40–45° C. for agar. Temperature sensitive additives, e.g. $GA_3$, BAP, and NAA, may be added to cooled, liquid, sterile media. Preferably these additives are filter sterilized prior to addition. $GA_3$, BAP, and NAA are preferably sterilized using filters having a pore size of about 0.22 μm.

The media may be dispensed into petri plates using standard aseptic techniques. Aliquots of media for 10 cm×2 cm petri plates may be about 30 mL.

Upon emergence of the hypocotyl, plants may be transferred to a first medium. These plants may then be incubated (a) in darkness at about 30° C., (b) in darkness at diurnal temperatures of about 30° C. and 20° C., or (c) under a 16 hr light/8 hr dark photoperiod at 20° C. The germination rate and duration of plants grown under constant temperature and diurnal temperatures may be monitored. Synchronization may be assessed by comparing epicotyl differentiation, coleoptile emergence and radicle emergence.

Secondary explants obtained from germinating seeds having an epicotyl with an emergent coleoptile and having a radicle with an emergent hypocotyl may be transferred under aseptic conditions to a new petri plate. The media in this new plate may be a second (leafing) media. Transferred plants may be incubated in an environment having about 16-hr days under about 2000 lux of light and about 8-hr nights in total darkness at a constant temperature of 20° C. Illumination may be provided by 40-watt cool, white fluorescent tubes. Emergence of the first foliage leaf from explants may be monitored.

Upon emergence of a first foliage leaf, secondary explants may be transferred under aseptic conditions to a new petri plate. The media in this new plate may be a third (budding) media. Transferred plants may be incubated in an environment having from about 6-hr to about 10-hr days under about 2000 lux of light and from about 18-hr to about 14-hr nights in total darkness at a constant temperature of 20° C. Illumination may be provided by 40-watt cool, white fluorescent tubes. Emergence of the first foliage leaf from explants may be monitored. The humidity may be maintained at 50–60% RH. Plants may be periodically subcultured onto fresh third media, e.g. every four weeks. The appearance of de novo axillary buds may be monitored as well as the appearance of foliage leaves from such buds.

The final data from periodic observations may be compiled after about 16 weeks of culture.

In some embodiments of the invention, transfer of seeds with emerged hypocotyl to a first basal culture medium and incubation at 20° C. (+20° C.) under 8–16 hr photoperiod (2000–3500 lux) results in the release of epicotyl, coleoptile and radicle within 81 days of incubation of seeds.

In still another embodiment of the present invention, a synergistic formulation used for induction of germination and release of epicotyl, coleoptile and radicle dormancy in seeds of *Polygonatum cirrhifolium* at temperature range of 28–32° C. and diurnal temperature range of 28–32/18–22° C. under darkness for induction of hypocotyl. In other embodiments, the temperature range is 18–22° C. under 8–16 hr photoperiod (light intensity 2000–3500 lux) for induction of epicotyl, coleoptile and radicle.

According to preferred embodiments of the invention, the humidity is maintained between about 50% and about 60% relative humidity.

According to some preferred embodiments of the invention, plants maintained at 20–24° C. under a 10–16 hr photoperiod (2000–3500 lux) at 50–60% relative humidity (RH) on set 1 or set 2 media release first foliage leaves from the emergent coleoptile. In addition, de novo axillary bud differentiation and sprouting are observed on plants on set 2 media.

Release of epicotyl dormancy in vitro in *P. cirrhifolium* is supported when cultivated according to the invention at a temperature of from about 20° C. to about 24° C. Release of epicotyl dormancy in vitro in *P. cirrhifolium* is also supported when cultivated according to the invention under from about a 10 to about a 16 hr photoperiod at a light intensity of 2000–3500 lux. Release of epicotyl dormancy in vitro in *P. cirrhifolium* is also supported when cultivated according to the invention at a relative humidity of from about 50% to about 60%.

In preferred embodiments of the invention, the first (germination), second (leafing), and third (budding) media are used consecutively in increasing numerical order.

EXAMPLES

The present invention is illustrated, but not limited, by the following examples. Other examples and embodiments will be apparent to those skilled in the art and do not depart from the spirit and scope of the invention.

Ripe purplish berries from plants grown in the wild were collected and dehydrated for 15 days at room temperature (29° C.±2° C.). Seeds were collected from dehydrated berries and washed in tap water with 1–2 drops of Tween-20™ for 2 hours and rinsed three times in distilled water. Seeds were then surface sterilized with 0.1% mercuric chloride ($HgCl_2$) for 3 minutes. Mercuric chloride was removed by washing seeds four times in sterile distilled water. Sterilized, rinsed seeds were placed on semi-solid culture medium in sterile disposable plastic Petri plates (10 cm×2 cm).

Macro and micro nutrients in the basal medium were that of Murashige and Skoog's (Murashige, T. and Skoog, F. 1965. Physiol Plant 15: 433 –497) but modified to contain 2.2 g/L $NH_4NO_3$, 2.0 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$. This medium was supplemented with 250 mg/L myo-inositol, 0.5 mgl/l nicotinic acid, 0.5 mg/L pyridoxine HCl, 3 mg/L thiamine HCl, 2 mg/L glycine, 30 g/L sucrose, 7.5 g/L agar and 2, 10, 25, and 50 mg/L gibberellic acid.

The pH of the medium was adjusted to 5.8 before adding agar. Medium was sterilized at 121° C. (15 lb. psi pressure) for 20 minutes. $GA_3$ was incorporated after filter sterilization (0.22 μm pore cell, Millipore filter to cooled (40–45° C.) autoclaved medium. BAP and NAA were added prior to autoclaving. Medium was dispensed in culture tubes (25× 150 mm, Borosil) and conical vials (100 ml, Borosil) as 25 and 35 ml aliquots respectively.

Parafilm-sealed petri dishes were incubated in two separate growth chambers at a temperature of 30° C. (±2° C.; dark) and diurnal temperature of 30/20° C. (±2° C.; dark) at 50–60% relative humidity (RH).

Germination was evaluated every three days by examining seeds for hypocotyl emergence. Results were expressed as a percentage, i.e. number of seeds exhibiting a hypocotyl versus the total number of seeds. Seeds with emerged hypocotyl were transferred under aseptic conditions to the above defined basal culture medium containing gibberellic acid at 5, 25, 50 and 100 mg/L. Transferred plants were incubated in an environment having 8–16-hr days under about 2000 lux of light and about 8–16-hr nights in total darkness at a constant temperature of 20° C. (±20° C.) and at 50–60% RH. Illumination was provided by 40-watt cool, white fluorescent tubes. Germination synchronization as indicated by differentiated epicotyl with emergent coleoptile and radicle was recorded on daily basis.

Tables 1 and 2 show the induction of germination as indicated by the emergence of hypocotyl at temperature of 30° C. (±2° C.; dark; RH 50–60%) and diurnal temperature of 30/20° C. (±2° C.; dark; RH 50–60%).

The consequent step of synchronization of germination is presented in table 3 in which epicotyl with emergent coleoptile and radicle is manifest under 8–16 hr photoperiod (light intensity 2000–3500 lux) at an incubation temperature of 20° C. (RH 50–60%).

Cultures were maintained at 50–60% RH. Plants were subcultured every four weeks in both sets of experiments on the same media formulations. Observations were made periodically but final data was compiled after 16 weeks of culture.

Figure 2:
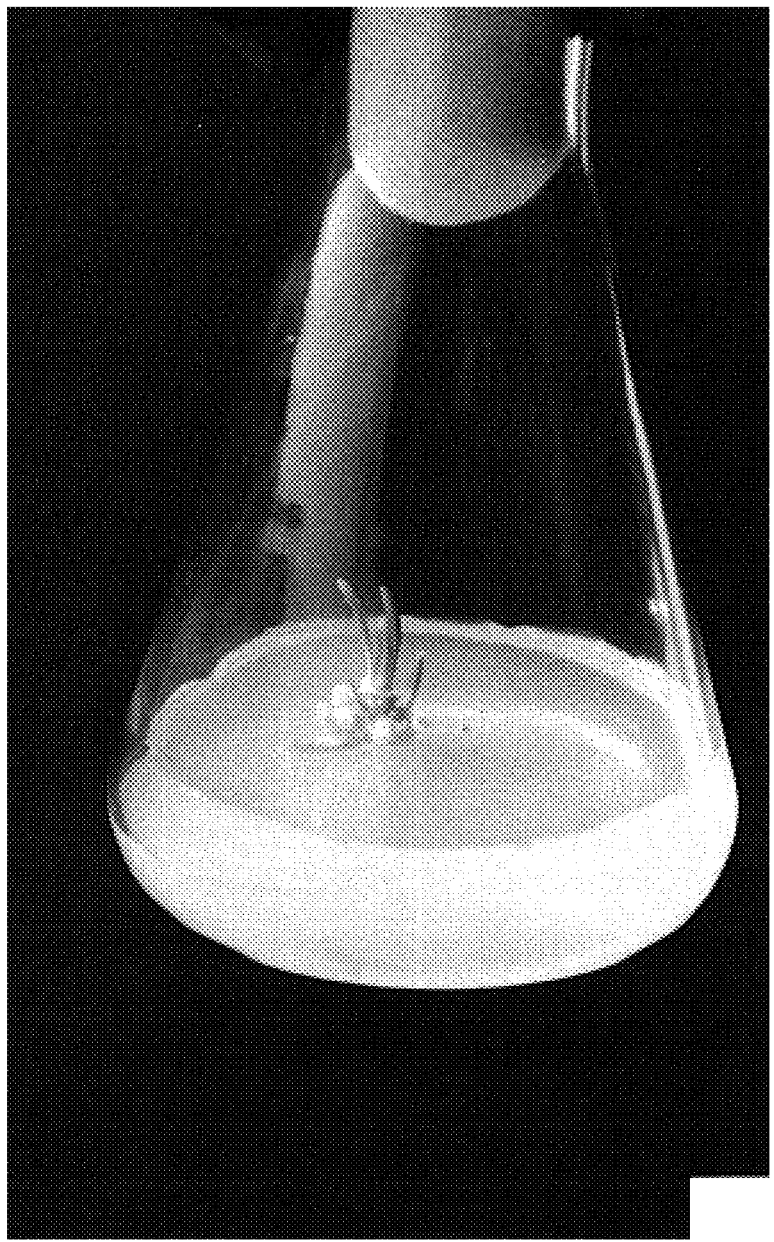
FIG. 2. Differentiated *Polygonatum cirrhifolium* Royle epicotyl with emerging radicle (ra) and coleoptile (col).
Figure 3:
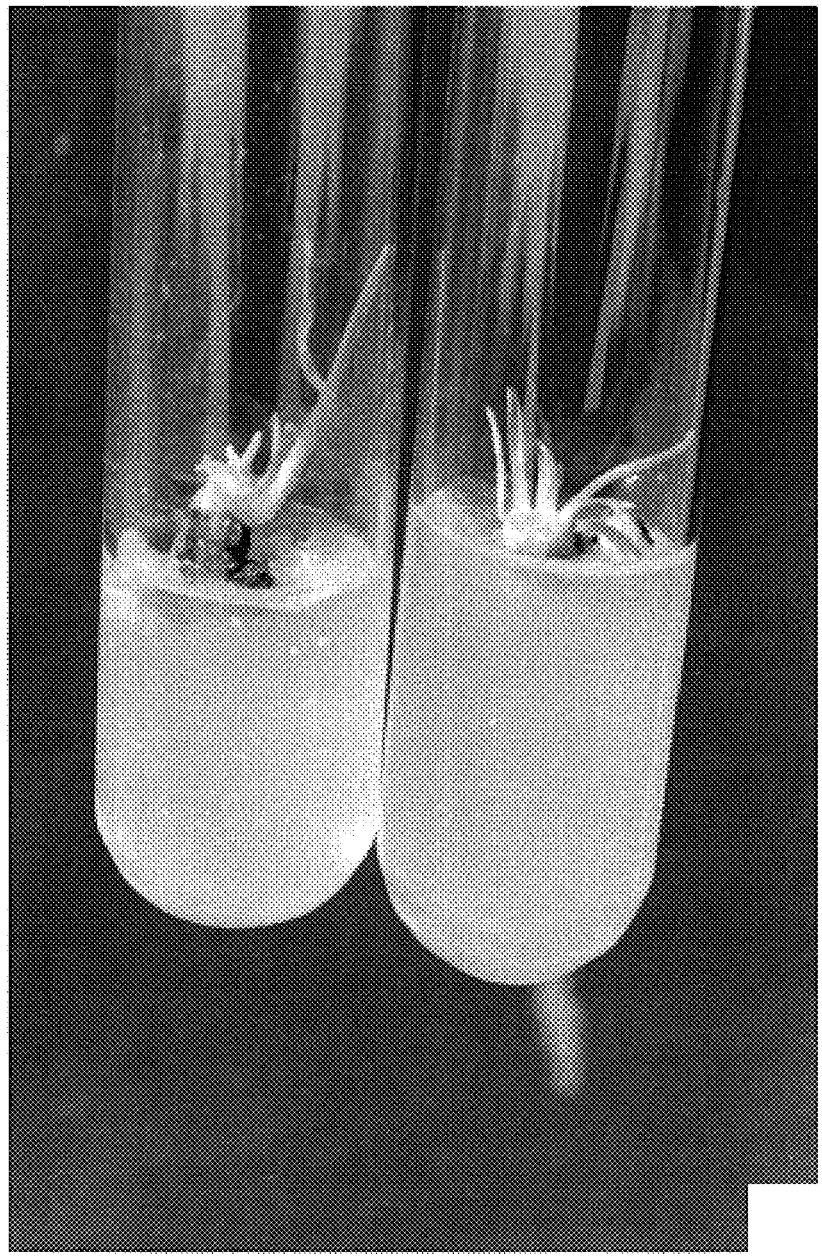
FIG. 3. Well differentiated *Polygonatum cirrhifolium* Royle coleoptile (col) with emergent radicle (ra) and coleoptile (col).
Figure 4:
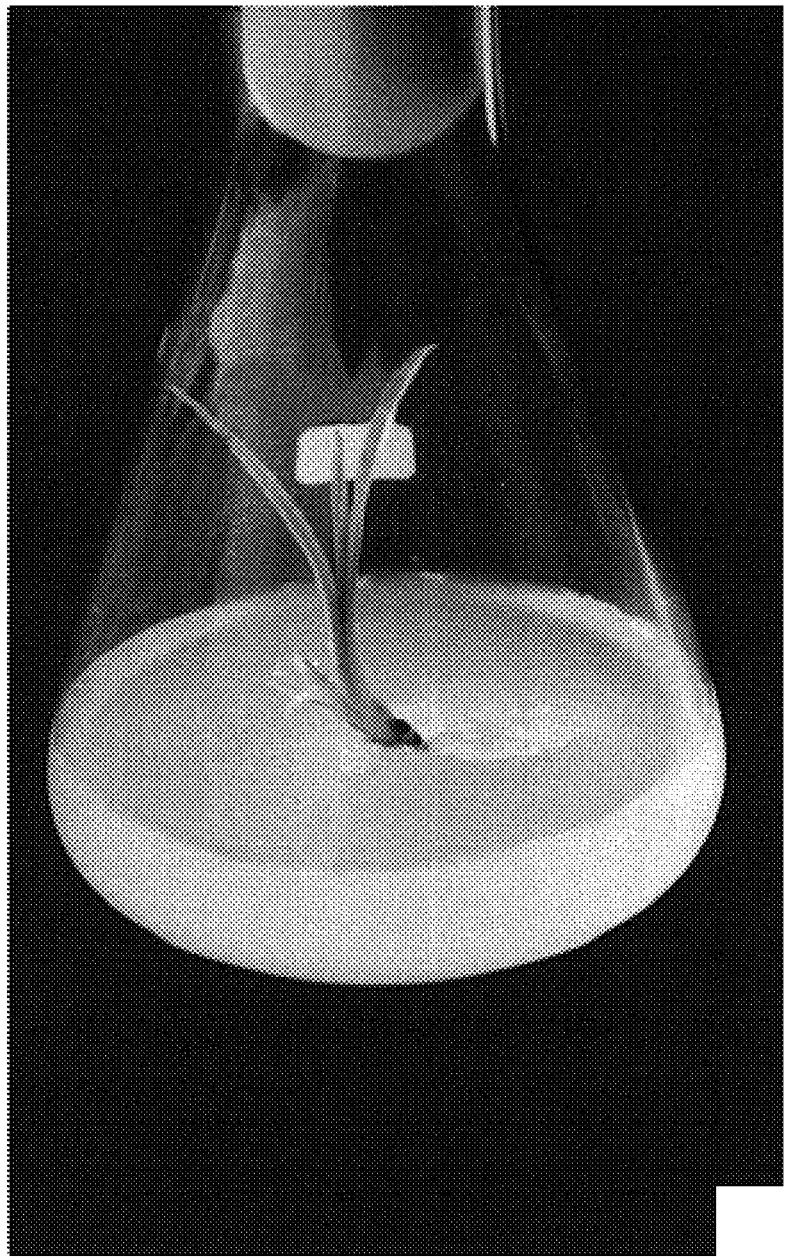
FIG. 4. Well differentiated *Polygonatum cirrhifolium* Royle coleoptile (col) with emergent radicle (ra) and coleoptile (col).
Figure 5:
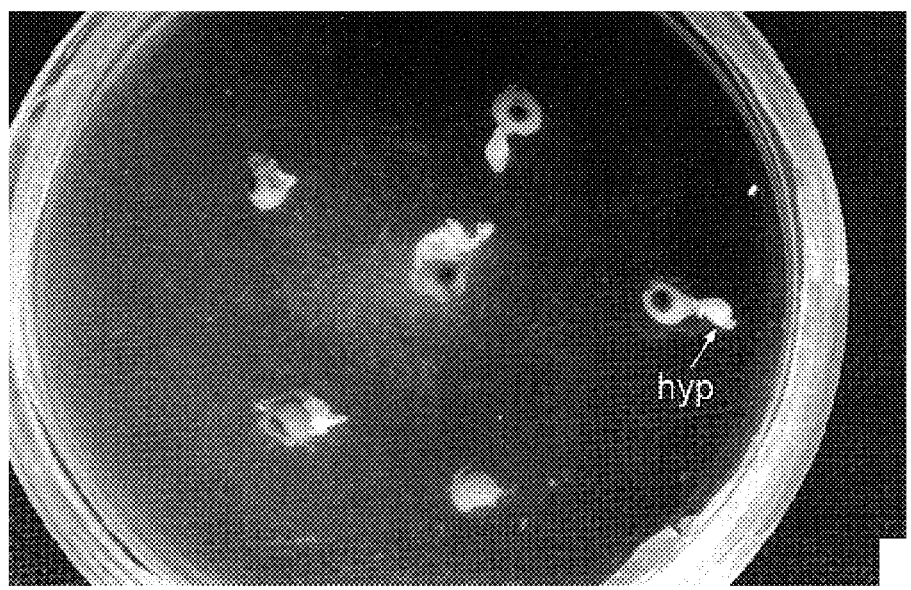
FIG. 5. Release of rosette of leaves from the coleoptile of *Polygonatum cirrhifolium* Royle.
Figure 6:
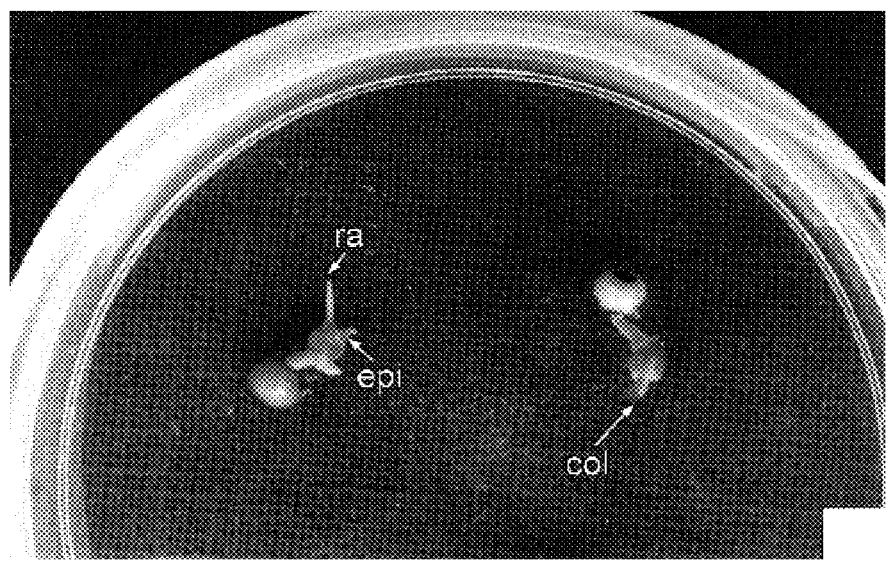
FIG. 6. Release of first foliage leaves and de novo differentiation of axillary buds from the rhizomatous base of *Polygonatum cirrhifolium* Royle.
Figure 7:
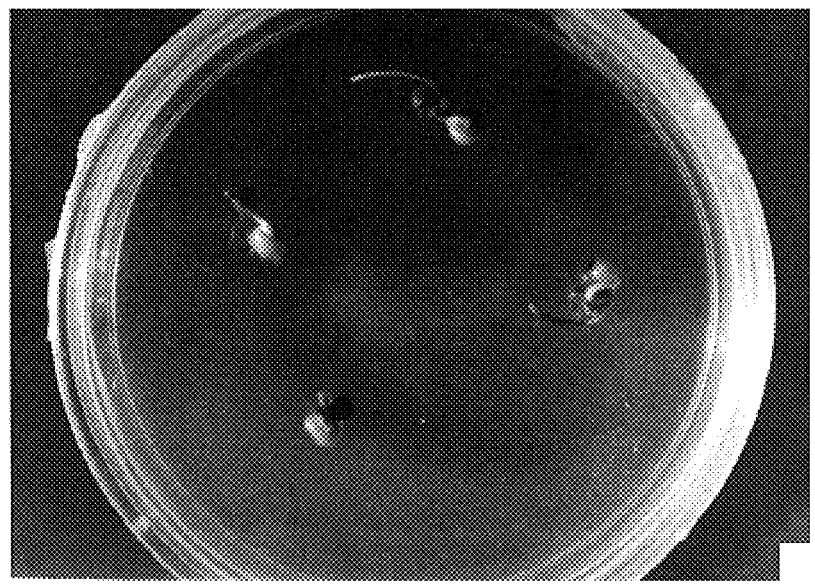
FIG. 7. Sprouting of axillary buds of *Polygonatum cirrhifolium* Royle.
Figure 8:
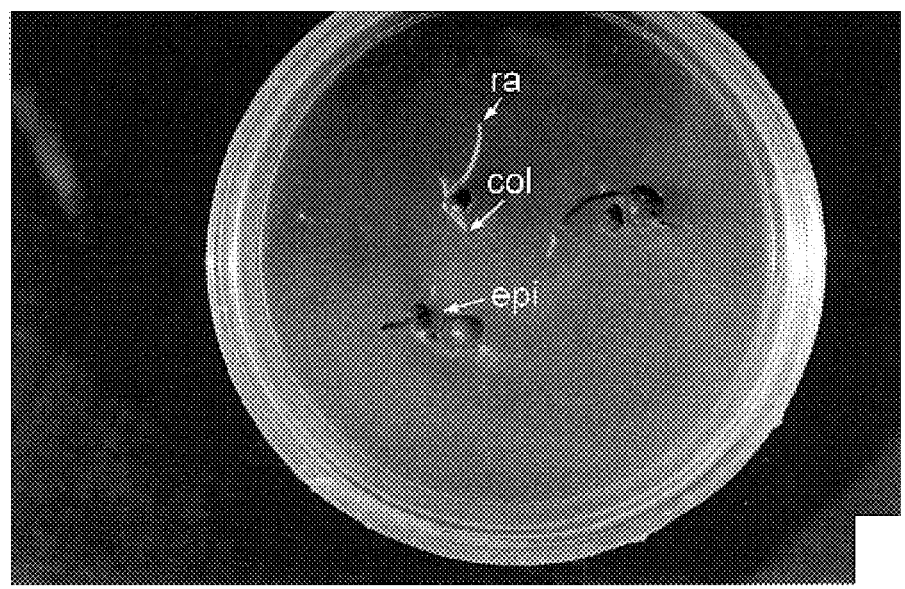
FIG. 8. Excised axillary bud with emergent leaves of *Polygonatum cirrhifolium* Royle.

In the diagram accompanying the specification FIG. 1 explains the release of rosette of leaves from the coleoptile. FIG. 2 shows the release of first foliage leaves and de novo differentiation of axillary buds from the rhizomatous base. FIG. 3 shows the sprouting of axillary buds and FIG. 4 depicts the excised axillary bud with emergent leaves.

In still another embodiment of the present invention, results in table 4 and 5 show the influence of various concentrations and combinations of BAP, NAA and $GA_3$ on the in vitro release of epicotyl dormancy indicated by the release of rosette of leaves and induction of de novo axillary bud differentiation and their sprouting at 20–24° C. under 10–16 hr photoperiod (2000–3500 lux) at 50–60% of RH.

Example 1

Experiment consisted of 4 treatments in the form of varying levels of $GA_3$ (2, 10, 25 and 50 mg/L) supplemented to culture medium consisting of 2.2 g/L $NH_4NO_3$, 2.0 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 250 mg/L myo-inositol, 0.5 mg/L nicotinic acid, 0.5 mg/L pyridoxine HCl, 3 mg/L thiamine HCl, 2 mg/L glycine, 30 g/L sucrose and 7.5 g/L agar.

Each treatment consisted of 15 replicates with 5 seeds in each. These were incubated at a constant temperature of 30° C. under continuous darkness at a RH of 60%. With the increase in $GA_3$ concentration, there is concomitant increase in germination (Table 1). Maximum germination of 98.53% was obtained at 25 mg/L of $GA_3$. Germination extended from 24–61 days (maximum duration) at 2 mg/L of $GA_3$ and 7–23 days (minimum duration) at 50 mg/L of $GA_3$ respectively.

TABLE 1

Effect of different levels of $GA_3$ supplemented to modified MS culture medium on germination percentage and duration of germination at 30° C. in dark

| $GA_3$ concentration (mg/L) | Percent germination | Duration of germination |
|---|---|---|
| 2 | 23.69 ± 7.04* | 24–61 |
| 10 | 66.18 ± 4.77 | 19–53 |
| 25 | 98.53 ± 3.82 | 11–30 |
| 50 | 97.11 ± 4.01 | 7–23 |

*Mean, ±S.E.

Example 2

In this experiment also there were 4 treatments with varying levels of $GA_3$ 2–50 mg/L. Supplemented to the modified MS basal culture medium containing of 2.2 g/L NH$_4$NO$_3$, 2.0 g/L KNO$_3$, 0.44 g/l CaCl$_2$.2H$_2$O, 0.37 g/L MgSO$_4$.7H$_2$O, 0.17 g/L KH$_2$PO$_4$, 37.25 mg/L Na$_2$ EDTA, 27.8 mg/L FeSO$_4$.7H$_2$O, 0.83 mg/L KI, 6.2 mg/L H$_3$BO$_3$, 22.3 mg/L MnSO$_4$.4H$_2$O, 8.6 mg/L ZnSO$_4$.7H$_2$O, 0.25 mg/L Na$_2$ MoO$_4$.2H$_2$O, 0.025 mg/L CuSO$_4$.5H$_2$O, 0.025 mg/L CoCl$_2$.6H$_2$O, 250 g/L myo-inositol, 0.5 mg/L nicotinic acid, 0.5 mg/L pyridoxine HCl, 3 mg/L thiamine HCl, 2 mg/L glycine, 30 g/L sucrose and 7.5 g/L agar. Cultures were incubated under diurnal temperature regime of 30/20° C. (dark). Each treatment consisted of 15 replicates with 5 seeds in each. Germination is induced in all the treatments (table 2). Maximum germination of 62.12% is obtained at 50 mg/L 0f GA$_3$.

TABLE 2

Effect of different levels of GA$_3$ supplemented to modified MS culture medium on germination percentage and duration of germination at 20/30° C. in dark

| GA$_3$ concentration (mg/L) | Percent germination | Duration of germination |
|---|---|---|
| 2 | 12.41 ± 6.17 | 32–73 |
| 10 | 18.06 ± 4.32 | 34–72 |
| 25 | 46.00 ± 5.11 | 27–63 |
| 50 | 62.12 ± 3.66 | 23–58 |

Example 3

In this experiment seeds with emerged hypocotyl were transferred to the culture to modified MS basal culture medium containing of 2.2 g/L NH$_4$NO$_3$, 2.0 g/L KNO$_3$, 0.44 g/l CaCl$_2$.2H$_2$O, 0.37 g/L MgSO$_4$.7H$_2$O, 0.17 g/L KH$_2$PO$_4$, 37.25 mg/L Na$_2$ EDTA, 27.8 mg/L FeSO$_4$.7H$_2$O, 0.83 mg/L KI, 6.2 mg/L H$_3$BO$_3$, 22.3 mg/L MnSO$_4$.4H$_2$O, 8.6 mg/L ZnSO$_4$.7H$_2$O, 0.25 mg/L Na$_2$MoO$_4$.2H$_2$O, 0.025 mg/L CuSO$_4$.5H$_2$O, 0.025 mg/L CoCl$_2$.6H$_2$O, 250 mg/L myo-inositol, 0.5 mg/L nicotinic acid, 0.5 mg/L pyridoxine HCl, 3 mg/L thiamine HCl, 2 mg/L glycine, 30 g/L sucrose and 7.5 g/L agar and supplemented with 4 concentrations of GA$_3$ viz. 10,25,50 and 100 mg/L. Cultures were incubated at 20° C. under 16 hr photoperiod in a growth chamber. there were four treatments in total and each treatment consisted of 15 replicates with 4 seeds with emerged hypocotyl in each replicate. The effect of various treatments on the release of epicotyl, coleoptile radicle and days to release/ synchronization is described in table 3.100 mg/L of GA$_3$ results in 100% synchronization after 11 days of culture.

TABLE 3

Effect of different levels of GA$_3$ supplemented to modified MS culture medium for The release of epicotyl, coleoptile radicle and days to synchronization.

| GA$_3$ concentration (mg/L) | Percent seeds with epicotyl, coleoptile & radicle | Days to release epicotyl, coleoptile & radicle |
|---|---|---|
| 10 | 23.71 ± 2.00 | 21 |
| 25 | 78.23 ± 3.11 | 18 |
| 50 | 100.00 ± 0.00 | 14 |
| 100 | 100.00 ± 0.00 | 11 |

The synergistic activity for the in vitro release of epicotyl dormancy in *P. cirrhifolium* indicated by the lease of rosette of leaves and differentiation of de novo axillary buds and their sprouting of the medium is presented in the following examples which may not be construed to limit the scope invention.

Example 4

Experiment consisted of 9 treatments in the form of various combinations of BAP (1–6 mg/L) and NAA (0.1–1.0 mg/L) supplemented to MS basal culture medium containing 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, 30 g/L sucrose, 7.0 g/L agar. Each treatment consisted of 24 cultures. These were incubated at 20° C. under 16 hr photoperiod (2000 lux) at 60% RH. Synergistic combination of BAP and NAA is effective at all levels (table 1). However BAP to NAA ratio of 3:1 yields the optimum response resulting in release of first foliage leaves in 85.15% of secondary explants. 6 mg/L of BAP in combination with 1 mg/L of NAA gave maximum number of leaves ( 3.40) and leaf length (5.56 cm) respectively.

TABLE 4

Influence of 3 levels of BAP in combination with 3 levels of NAA on the release of first foliage leaves cultured on MS medium (data from periodic observations compiled after 16 weeks of culture)

| BAP Concentrat- | Percentage secondary explants producing leaves NAA (mg/L) | | | Mean number of leaves per secondary explant NAA (mg/L) | | | Mean leaf length (cm) NAA (mg/L) | | |
|---|---|---|---|---|---|---|---|---|---|
| ion (mg/L) | 0.1 | 0.5 | 1.0 | 0.1 | 0.5 | 1.0 | 0.1 | 0.5 | 1.0 |
| 1.0 | 4.70 | 14.81 | 25.92 | 2.00 ± 0.13* | 2.25 ± 0.24 | 2.33 ± 0.16 | 2.11 ± 0.34 | 1.76 ± 0.27 | 2.71 ± 0.42 |
| 3.0 | 11.12 | 66.67 | 85.18 | 1.99 ± 0.16 | 2.74 ± 0.42 | 2.93 ± 0.31 | 2.03 ± 0.51 | 3.17 ± 0.83 | 3.08 ± 0.63 |
| 6.0 | 20.22 | 20.74 | 70.37 | 2.34 ± 0.43 | 3.01 ± 0.32 | 3.40 ± 0.41 | 3.71 ± 0.49 | 4.04 ± 0.99 | 5.56 ± 1.31 |

*S.E.

Example 5

In this experiment there were 5 treatments with varying levels of $GA_3$ (1–20 mg/L) in combination with 3 mg/L of BAP and 1.0 mg/L of NAA supplemented to MS basal culture medium containing 1.65 g/L $NH_4NO_3$; 1.9 g/L $KNO_3$, 0.44 g/l $CaCl_2.2H_2O$, 0.37 g/L $MgSO_4.7H_2O$, 0.17 g/L KH$_2$PO$_4$, 37.25 mg/L Na$_2$ EDTA, 27.8 mg/L FeSO$_4$.7H$_2$O, 0.83 mg/L KI, 6.2 mg/L H$_3$BO$_3$, 22.3 mg/L MnSO$_4$.4H$_2$O, 8.6 mg/L ZnSO$_4$.7H$_2$O, 0.25 mg/L Na$_2$MoO$_4$.2H$_2$O, 0.025 mg/L CuSO$_4$.5H$_2$O, 0.025 mg/L CoCl$_2$.6H$_2$O, 100 mg/L myo-inositol, 0.5 mg/L nicotinic acid, 0.5 mg/L pyridoxine HCl, 0.1 mg/L thiamine HCl, 2 mg/L glycine, 30 g/L sucrose, 7.0 g/L agar. Each treatment consisted of 24 cultures. These were incubated at 20° C. under 16 hr photoperiod (2000 lux) at 60% RH. Effect of various levels of GA$_3$ in combination with BAP (3 mg/L) and NAA (1.0 mg/L) on percentage of secondary explants producing axillary buds per explant and percentage of axillary buds producing leaves is described in table 5. There is a concomitant increase in the elicitation of response with the increasing concentrations of GA$_3$.

TABLE 5

Effect of various levels of GA$_3$ in combination with 2 mg/L of BAP and 1.0 mg/L of NAA on de novo axillary bud differentiation and the release of foliage leaves from them on MS medium (data from periodic observations compiled after 16 weeks of culture).

| GA3 concentration (mg/L) | Percentage secondary-explants producing axillary buds | Mean number of axillary buds per secondary explant | Percentage axillary buds producing leaves | Remarks |
|---|---|---|---|---|
| 1. | 16.67 | 2.70 ± 0.70* | 37.03 | Epicotylar bulge swells forms rhizomatous base |
| 5. | 70.83 | 6.44 ± 1.04 | 46.58— | — |
| 10. | 87.50 | 9.06 ± 2.00 | 66.22 | — |
| 15. | 100.00 | 11.67 ± 1.96 | 77.12 | — |
| 20. | 100.00 | 8.96 ± 2.01 | 97.03 | Rhizomatous base, callus induction |

*S.E.

The references cited throughout this application and listed below are incorporated herein in their entirety by reference.

We claim:

1. A method of in vitro cultivation of *Polygonatum* comprising the steps of:
   contacting a *Polygonatum* seed with a first medium comprising a MS basal culture medium and gibberellic acid (GA$_3$) present in an amount from about 10 mg/L to about 100 mg/L;
   upon emergence of a hypocotyl of a seedling, contacting said seedling with a second medium comprising a MS basal culture medium, 6-benzyl-aminopurine present in an amount from about 3 mg/L to about 6 mg/L, and naphthalene acetic acid (NAA) present in an amount from 0.5 mg/L to about 1.0 mg/L; and
   upon emergence of a first foliage leaf of said seedling, contacting said seedling with a third medium comprising a MS basal culture medium, 6-benzyl-aminopurine present in an amount of about 2.0 mg/L, naphthalene acetic acid present in an amount of about 1.0 mg/L, and GA$_3$ present in an amount from about 5 mg/L to about 20 mg/L,
   wherein the MS basal culture medium is selected from the group consisting of MS basal culture medium I and MS basal culture medium II, wherein MS basal culture medium I comprise 2.2 g/L NH$_4$NO$_3$, 2.0 g/L KNO$_3$, 0.44 g/l CaCl$_2$.2H$_2$O, 0.37 g/L MgSO$_4$.7H$_2$O, 0.17 g/L KH$_2$PO$_4$, 37.25 mg/L Na$_2$ EDTA, 27.8 mg/L FeSO$_4$.7H$_2$O, 0.83 mg/L KI, 6.2 mg/L H$_3$BO$_3$, 22.3 mg/L MnSO$_4$.4H$_2$O, 8.6 mg/L ZnSO$_4$.7H$_2$O, 0.25 mg/L Na$_2$ MoO$_4$.2H$_2$O, 0.025 mg/L CuSO$_4$.5H$_2$O, 0.025 mg/L CoCl$_2$.6H$_2$O, 250 mg/L myo-inositol, 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L NH$_4$NO$_3$, 1.9 g/L KNO$_3$, 0.44 g/l CaCl$_2$.2H$_2$O, 0.37 g/L MgSO$_4$.7H$_2$O, 0.17 g/L KH$_2$PO$_4$, 37.25 mg/L Na$_2$ EDTA, 27.8 mg/L FeSO$_4$.7H$_2$O, 0.83 mg/L KI, 6.2 mg/L H$_3$ BO$_3$, 22.3 mg/L MnSO$_4$.4H$_2$O, 8.6 mg/L ZnSO$_4$.7H$_2$O, 0.25 mg/L Na$_2$ MoO$_4$.2H$_2$O, 0.025 mg/L CuSO$_4$.5H$_2$O, 0.025 mg/L CoCl$_2$.6H$_2$O, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

2. The method of claim 1, wherein the *Polygonatum* is selected from the group consisting of *Polygonatum cirrhifolium*, *Polygonatum oppositifolium*, and *Polygonatum verticillatum* L.

3. The method of claim 2, wherein the *Polygonatum cirrhifolium*, is *Polygonatum cirrhifolium* Royle.

4. The method of claim 2, wherein the *Polygonatum oppositifolium*, is *Polygonatum oppositifolium* Royle.

5. The method of claim 1, wherein GA$_3$ in the first medium is present in an amount from about 50 mg/L to about 100 mg/L.

6. The method of claim 1, wherein NAA in the second medium is present in an amount of about 1.0 mg/L.

7. The method of claim 1, wherein GA$_3$ in the third medium is present in an amount from about 15 mg/L to about 20 mg/L.

8. The method of claim 1, wherein the MS basal culture medium of the first, second, and/or third medium is MS basal culture medium I.

9. The method of claim 1, wherein the MS basal culture medium of the first, second, and/or third medium is MS basal culture medium II.

10. The method of claim 1, wherein the first, second, and/or third medium further comprises agar.

11. The method of claim 1, wherein the MS basal culture medium of the first, second, and/or third medium has a pH of about 5.8.

12. The method of claim 1, wherein said contacting steps are performed at a temperature is from about 20° C. to about 24° C.

13. The method of claim 1, wherein said contacting steps are performed at a relative humidity about 50% to about 60%.

14. The method of claim 1, wherein said *Polygonatum* is contacted with said first medium in the absence of light.

15. The method of claim 1, wherein said *Polygonatum* is contacted with said second and/or third medium under illumination of about 2000 to about 3500 lux.

16. The method of claim 1, wherein the primary explant is contacted with the second medium less than 60 days after said seeds are contacted with the first medium.

17. A method of in vitro cultivation of *Polygonatum cirrhifolium* Royle comprising the steps of
   contacting a *Polygonatum cirrhifolium* Royle seed with a first medium comprising a MS basal culture medium and gibberellic acid (GA$_3$) present in an amount from about 10 mg/L to about 100 mg/L;
   upon emergence of a hypocotyl of a seedling, contacting said seedling with a second medium comprising a MS basal culture medium, 6-benzyl-aminopurine present in an amount from about 3 mg/L to about 6 mg/L, and naphthalene acetic acid (NAA) present in an amount from 0.5 mg/L to about 1.0 mg/L; and upon emergence of a first foliage leaf of said seedling, contacting said seedling with a third medium comprising a MS basal culture medium, 6-benzyl-aminopurine present in an amount about 2.0 mg/L, NAA present in an amount about 1.0 mg/L, and $GA_3$ present in an amount from about 5 mg/L to about 20 mg/L.

wherein the steps are performed at a temperature from about 20° C. to about 24° C., and the relative humidity is about 50% to about 60%, wherein the second medium is contacted with the seedling less than 60 days after said seeds are contacted with the first medium, and the seedling is contacted with the third medium less than 90 days after said seeds are contacted with the first medium, wherein the MS basal culture medium is selected from the group consisting of MS basal culture medium I and MS basal culture medium II, wherein MS basal culture medium I comprises 2.2 g/L $NH_4NO_3$, 2.0 g/L $KNO_3$, 0.44 g/L $CaCl_2 \cdot 2H_2O$, 0.37 g/L $MgSO_4 \cdot 7H_2O$, 0.17 g/L $KH_2PO_4$, 37.25 mg/L $Na_2$ EDTA, 27.8 mg/L $FeSO_4 \cdot 7H_2O$, 0.83 mg/L KI, 6.2 mg/L $H_3BO_3$, 22.3 mg/L $MnSO_4 \cdot 4H_2O$, 8.6 mg/L $ZnSO_4 \cdot 7H_2O$, 0.25 mg/L $Na_2MoO_4 \cdot 2H_2O$, 0.025 mg/L $CuSO_4 \cdot 5H_2O$, 0.025 mg/L $CoCl_2 \cdot 6H_2O$, 250 mg/L myo-inositol, 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4 \cdot 4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

18. A method of germinating *Polygonatum* seeds comprising contacting a plurality of *Polygonatum* seeds with a first medium comprising a MS basal culture medium and gibberellic acid ($GA_3$) present in an amount from about 10 mg/L to about 100 mg/L wherein 65–100% of the seeds are germinated and wherein germination occurs in less than 60 days wherein the MS basal culture medium is selected from the group consisting of MS basal culture medium I and MS basal culture medium II, wherein MS basal culture medium I comprises 2.2 g/L $NH_4NO_3$, 2.0 g/L $KNO_3$, 0.44 g/L $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 250 mg/L myo-inositol, 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

19. The method of claim 12, wherein $GA_3$ in said first medium is present in an amount of about 50 mg/L, and wherein 98% of the seeds generate a seedling.

20. A method of germinating *Polygonatum* seeds comprising contacting a plurality of *Polygonatum* seeds with a first medium comprising a MS basal culture medium and gibberellic acid ($GA_3$) present in an amount from about 50 mg/L wherein 65–100% of said *Polygonatum* seeds germinate in less than 60 days, wherein the MS basal culture medium is selected from the group consisting of MS basal culture medium I and MS basal culture medium II, wherein MS basal culture medium I comprises 2.2 g/L $NH_4NO_3$, 2.0 g/L $KNO_3$, 0.44 g/L $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 250 mg/L myo-inositol, 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

21. The method of claim 14, wherein $GA_3$ in said first medium is present in an amount of about 50 mg/L and wherein 98% of the seeds generate a seedling.

22. A method of inducing synchronous release of epicotyl dormancy, coleoptile dormancy, and radicle dormancy in *Polygonatum* comprising contacting a hypocotyl-bearing *Polygonatum* seed with a medium comprising a MS basal culture medium, 6-benzyl-aminopurine present in an amount from about 3 mg/L to about 6 mg/L, and naphthalene acetic acid present in an amount from 0.5 mg/L to about 1.0 mg/L, wherein the MS basal culture medium is selected from the group consisting of MS basal culture medium I and MS basal culture medium II, wherein MS basal culture medium I comprises 2.2 g/L $NH_4NO_3$, 2.0 g/L $KNO3$, 0.44 g/L $CaCl_2. 2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 250 mg/L myo-inositol, 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

23. A method for fast and synchronized in vitro induction of germination in *Polygonatum cirrhifolium* Royle, said method comprising:

a. obtaining the seeds from plant *Polygonatum cirrhifolium* Royle, wherein the seeds are sterilized, b. placing the sterilized seeds in sterile disposable plastic Petri plates (10×2 cm) containing semi-solid culture medium with 7.5% agar, c. incubating the petri dishes at temperature ranging between 20 to 24° C. and at a relative humidity (RH) ranging between 50 to 60%, wherein the petri dishes are parafilm sealed, d. transferring said seeds with emerged hypocotyl under aseptic conditions using Laminar Air Flow, to first medium culture comprising Murashige and Skoog's (MS) basal culture medium, and Gibberellic acid ($GA_3$) present in an amount ranging between 10 to 100 mg/L, e. incubating one set of said first medium culture at 30° C. under continuous dark conditions, f. incubating a second set of said first medium culture under diurnal temperature regime of 30/20° C., and continuous dark conditions, and g. transferring the said germinating seeds to a third set of first medium culture at 20° C. under 16 hours photoperiod in a growth chamber, wherein said first medium culture has a pH adjusted to 5.8 with 1N NaOH or 1N HCl, is sterilized for 20 minutes at 121° C. and 15 lb. psi pressure, comprises $GA_3$ incorporated into said medium after filter sterilization using 0.22 μm pore size filter to cooled autoclaved medium and dispensed into petri dishes as 30 ml aliquots and wherein the MS basal culture medium is selected from the group consisting of MS basal culture medium I and MS basal culture medium II, wherein MS basal culture medium I comprises 2.2 g/L $NH_4NO_3$, 2.0 g/L $KNO_3$, 0.44 g/L $CaCl_2.2H_2O$, 0.37 g/L $MgSO_4.7H_2O$, 0.17 g/L $KH_2PO4$, 37.25 mg/L $Na_2$ EDTA, 27.8 mg/L $FeSO_4.7H_2O$, 0.83 mg/L KI, 6.2 mg/L $H_3$ $BO_3$, 22.3 mg/L $MnSO_4.4H_2O$, 8.6 mg/L $ZnSO_4.7H_2O$, 0.25 mg/L $Na_2$ $MoO_4.2H_2O$, 0.025 mg/L $CuSO_4.5H_2O$, 0.025 mg/L $CoCl_2.6H_2O$, 250 mg/L myo-inositol, 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3$ $BO_3$, 22.3 mg/L $MnSO_4.4H_2O$, 8.6 mg/L $ZnSO_4.7H_2O$, 0.25 mg/L $Na_2$ $MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

24. The method of claim 23, wherein between 65 to 98% of the seeds are germinated, within a period of between 7 to 53 days, and wherein between 78 to 100% of seeds release epicotyl, coleoptile and radicle within between 11 to 18 days.

25. The method of claim 23, wherein about 98% of the seed are germinated within between 7 to 23 days, said composition comprises about 50 mg/L of $GA_3$.

26. The method of claim 23, wherein about 100% of the seeds release the epicotyl, coleoptile and radicle between 11 to 14 days, said composition comprising $GA_3$ in an amount between 50 to 100 mg/L.

27. The method of claim 23, wherein germination of seeds occurs in vitro within 81 day.

28. The method of claim 23, wherein said first medium further comprises plant hormones selected from the group consisting of alpha-naphthalene acetic acid (NAA), and 6-benzyl-aminopurine (BAP).

29. The method of claim 23, further comprising washing the seeds thoroughly for 2 hours under tap water with 1-2 drops of Tween-20™ and rinsing with distilled water.

30. The method of claim 24, wherein the seeds are sterilized with 0.1% mercuric chloride ($HgCl_2$).

31. A method for inducing release of epicotyl dormancy in *Polygonatum cirrhifolium* Royle comprising:

a. preparing a medium composition comprising MS basal culture medium, 6-benzyl-aminopurine (BAP) present in an amount ranging between 3 to 6 mg/L, and naphthalene acetic acid (NAA) present in an amount ranging between 0.5 to 1.0 mg/L, b. adjusting pH of the medium to 5.8 with 1N NaOH or 1N HCl, c. sterilizing the medium for 20 minutes at 121° C. and 15 lb. psi pressure, d. dispensing the medium into petri dishes as 30 ml aliquots, e. transferring seedlings consisting of epicotyl with emergent coleoptile and radicle obtained, from said germinating seeds, under aseptic conditions, into the said dishes, using Laminar Air Flow, and f. incubating the said dishes at 20° C. under 16 hr photoperiod with light intensity of 2000 lux provided by cool, white fluorescent tubes of 40 watts, wherein the MS basal culture medium is selected from the group consisting of MS basal culture medium I and MS basal culture medium II, wherein MS basal culture medium I comprises 2.2 g/L $NH_4NO_3$, 2.0 g/L $KNO_3$, 0.44 g/L $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3$ $BO_3$, 22.3 mg/L $MnSO_4.4H_2O$, 8.6 mg/L $ZnSO_4.7H_2O$, 0.25 mg/L $Na_2$ $MoO_4.2H_2O$, 0.025 mg/L $CuSO_4.5H_2O$, 0.025 mg/L $CoCl_2.6H_2O$, 250 mg/L myo-inositol. 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3BO_3$, 22.3 mg/L $MnSO_4.4H_2O$, 8.6 mg/L $ZnSO_4.7H_2O$, 0.25 mg/L $Na_2$ $MoO_4.2H_2O$, 0.025 mg/L $CuSO_4.5H_2O$, 0.025 mg/L $CoCl_2.6H_2O$, 100 mg/L, myo-inositol, 0.5 mg/L nicotinic acid, 0.5 mg/L pyridoxine HCl, 0.1 mg/L thiamine HCl, 2 mg/L glycine, and 30 g/L sucrose.

32. The method of claim 31, wherein between 65 to 86% of the seedlings produce leaves, said seedlings exhibiting a mean number of leaves ranging between 2.7 to 4, and a mean leaf length ranging between 3 to 6 cms.

33. The method of claim 31, wherein about 86% of the seedlings produce leaves, said seedlings exhibit a mean number of leaves of about 3.4 per seedling, and a mean leaf length of about 6 cms, wherein said composition comprises NAA present in an amount of about 1.0 mg/L.

34. The method of claim 31, wherein said composition further comprises plant hormones selected from the group consisting of gibberellic acid ($GA_3$), alpha-naphthalene acetic acid (NAA), and 6-benzyl-aminopurine (BAP).

35. The method of claim 31, further comprising washing seeds used to produce the seedlings thoroughly for 2 hours under tap water with 1–2 drops of Tween-20™ and rinsing the seeds with distilled water.

36. The method of claim 35, wherein said rinsed seeds are sterilized with 0.1% mercuric chloride ($HgCl_2$).

37. A method for inducing release of epicotyl dormancy from differentiated de novo axillary bud and release of foliage leaves in *Polygonatum cirrhifolium* Royle, comprising:

a. preparing a medium composition comprising MS basal culture medium, 6-benzyl-aminopurine (BAP) present in an amount about 2.0 mg/L, naphthalene acetic acid (NAA) present in an amount about 1.0 mg/L, and gibberellic acid ($GA_3$) present in an amount ranging between 5 to 20 mg/L, wherein $GA_3$ is incorporated into MS basal culture medium containing NAA and BAP after filter sterilization using a 0.22 mm pore size filter to cooled autoclaved medium, b. transferring seedlings comprising epicotyl with emergent coleoptile and radicle obtained from germinating seeds incubated under aseptic conditions using Laminar Air Flow, c. incubating the said seedlings at about 20° C. under duration ranging between 10 to 6 hr photoperiod, with light intensity of about 2000 lux, d. maintaining the seedlings at 50–60% relative humidity, e. subculturing the seedlings after every four weeks onto fresh medium compositions, wherein the MS basal culture medium is selected from the group consisting of MS basal culture medium I and MS basal culture medium II, wherein MS basal culture medium I comprises 2.2 g/L $NH_4NO_3$, 2.0 g/L $KNO_3$, 0.44 g/L $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3 BO_3$, 22.3 mg/L $MnSO_4.4H_2O$, 8.6 mg/L $ZnSO_4.7H_2O$, 0.25 mg/L $Na_2 MoO_4.2H_2O$, 0.025 mg/L $CuSO_4.5H_2O$, 0.025 mg/L $CoCl_2.6H_2O$, 250 mg/L myo-inositol, 0.5 mg/L nicotinic acid, 0.5 mg/L pyridoxine HCl, 3 mg/L thiamine HCl, 2 mg/L glycine, and 30 g/L sucrose and MS basal culture medium II comprises 1.65 g/L $NH_4NO_3$, 1.9 g/L $KNO_3$, 0.44 g/l $CaCl_2.2H_2O$, 0.37 g/L $MgSO_4.7H_2O$, 0.17 g/L $KH_2PO_4$, 37.25 mg/L $Na_2$ EDTA, 27.8 mg/L $FeSO_4.7H_2O$, 0.83 mg/L KI, 6.2 mg/L $H_3 BO_3$, 22.3 mg/L $MnSO_4.4H_2O$, 8.6 mg/L $ZnSO_4.7H_2O$, 0.25 mg/L $Na_2 MoO_4.2H_2O$, 0.025 mg/L $CuSO_4.5H_2O$, 0.025 mg/L $CoCl_2.6H_2O$, 100 mg/L myo-inositol, 0.5 mg/L nicotinic acid, 0.5 mg/L pyridoxine HCl, 0.1 mg/L thiamine HCl, 2 mg/L glycine, and 30 g/L sucrose.

38. The method of claim 37, wherein between 70 to 100% of the seedlings produce axillary buds, said seedlings exhibiting a mean number of axillary buds per explant ranging between 6 to 12, and wherein between 45 to 98% of said axillary buds produce leaves.

39. The method of claim 37 wherein about 100% of the seedlings producing axillary buds, number of axillary buds per seedling ranging between 9 to 12, and wherein between 77 to 98% of said axillary buds produce leaves, said composition comprises $GA_3$ present in an amount ranging between 15 to 20 mg/L.

40. The method of claim 37, further comprising washing seeds used to produce the seedlings thoroughly for 2 hours under tap water with 1–2 drops of Tween-20™ and rinsing the seeds with distilled water.

41. The method of claim 40, wherein said rinsed seeds are sterilized with 0.1% mercuric chloride ($HgCl_2$).

* * * * *